United States Patent
Kikuchi et al.

(10) Patent No.: US 9,097,688 B2
(45) Date of Patent: Aug. 4, 2015

(54) METHOD AND DEVICE FOR MEASURING WATER CONTENT IN HYDROGEN FLUORIDE-CONTAINING FLUORIDE SALT COMPOUNDS

(75) Inventors: Akiou Kikuchi, Ube (JP); Nobuyuki Tokunaga, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 498 days.

(21) Appl. No.: 13/581,424

(22) PCT Filed: Feb. 21, 2011

(86) PCT No.: PCT/JP2011/053663
§ 371 (c)(1),
(2), (4) Date: Aug. 27, 2012

(87) PCT Pub. No.: WO2011/108384
PCT Pub. Date: Sep. 9, 2011

(65) Prior Publication Data
US 2012/0322158 A1   Dec. 20, 2012

(30) Foreign Application Priority Data
Mar. 1, 2010   (JP) .................................. 2010-044146

(51) Int. Cl.
G01N 33/18 (2006.01)
G01N 25/56 (2006.01)
G01N 31/00 (2006.01)

(52) U.S. Cl.
CPC .................................... G01N 31/007 (2013.01)

(58) Field of Classification Search
USPC ......... 422/68.1, 78, 80; 436/39–42, 155, 157, 436/181
See application file for complete search history.

(56) References Cited

U.S. PATENT DOCUMENTS 3,607,076 A * 9/1971 Paine et al. ..................... 436/39
3,607,080 A * 9/1971 Paine et al. ..................... 436/39

(Continued)

FOREIGN PATENT DOCUMENTS

| | | |
|---|---|---|
| JP | 61-71356 A | 4/1986 |
| JP | 2-234056 A | 9/1990 |
| JP | 4-56789 A | 2/1992 |

(Continued)

OTHER PUBLICATIONS

Corresponding International Search Report with English Translation dated Mar. 29, 2011 ( five (5) pages).

(Continued)

*Primary Examiner* — Arlen Soderquist
(74) *Attorney, Agent, or Firm* — Crowell & Moring LLP

(57) ABSTRACT

The present invention provide a water content measurement method for a hydrogen fluoride-containing compound represented by the general formula: XF.nHF (where X is either one of K, $NH_4$, Na and Li; and n is a rational number greater than 0), including the steps of causing thermal decomposition of the hydrogen fluoride-containing compound, thereby generating a thermal decomposition gas, and then, determining the water content of the hydrogen fluoride-containing compound by quantification of the water content of the thermal decomposition gas. By this measurement method, it is possible to accurately quantify the content of water in the hydrogen fluoride-containing compound XF.nHF.

6 Claims, 2 Drawing Sheets

(56) References Cited

U.S. PATENT DOCUMENTS 3,847,554 A * 11/1974 Su .................................. 422/80
4,802,957 A * 2/1989 Kuwata et al. ................ 205/788

FOREIGN PATENT DOCUMENTS

| | | |
|---|---|---|
| JP | 5-281121 A | 10/1993 |
| JP | 5-281170 A | 10/1993 |
| JP | 8-101145 A | 4/1996 |
| JP | 2004-333413 * | 11/2004 |
| JP | 2006-308502 A | 11/2006 |

OTHER PUBLICATIONS

Form PCT/ISA/237 (four (4) pages).
Quantification of Water Content, Tokyo Kagaku Dojin, First Edition, (two (2) pages).
"Microchemical Water Content Analysis of Anhydrous Hydrofluoric Acid Based on Electric Conductivity Measurement", Miki and Maeno; Analytical Chemistry, vol. 29, No. 288, (1980), (four (4) pages).
"Anhydrous Hydrogen Fluoride for Industrial Use—Determination of Water Content—Conductimetric Method", International Standard ISO/DIS 3700.2, (1980) (ten (10) pages).

* cited by examiner

METHOD AND DEVICE FOR MEASURING WATER CONTENT IN HYDROGEN FLUORIDE-CONTAINING FLUORIDE SALT COMPOUNDS

TECHNICAL FIELD

The present invention relates to a method and device for quantifying the content of water in a hydrogen fluoride-containing compound.

BACKGROUND ART

As water content quantification methods for solid material samples, there are known: so-called heating method of heating a solid sample at a temperature slightly higher than a boiling point (100° C.) of water and determining the content of water in the sample based on the amount of weight decrease of the sample; and so-called dry method of storing and drying a solid sample, together with a water adsorbing agent such as molecular sieve, silica gel or calcium chloride, in a desiccator and determining the content of water in the sample based on the amount of weight increase of the absorbing agent (see Non-Patent Document 1). There are also widely known: Karl Fischer method for water content determination of solid and liquid samples; a method for water content determination of gas samples by an infrared spectroscope; and a method for water content determination of liquid samples by electric conductivity measurement.

The Karl Fischer method utilizes quantitative reaction of water in the presence of a lower alcohol such as methanol and an organic base such as pyridine as in the reaction scheme (A) and, upon generation of iodine by electrolysis of an electrolytic solution containing iodine ions as in the reaction scheme (B), detects the consumption of the iodine at a detection electrode by reaction with water. As $H_2O$ and $I_2$ react at a 1:1 ratio in the reaction scheme (A), the water content of the sample is quantified based on the quantity of electricity required for the electrolysis in the Karl Fischer method.

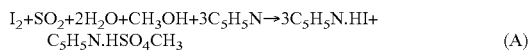

$I_2+SO_2+2H_2O+CH_3OH+3C_5H_5N \rightarrow 3C_5H_5N.HI+ C_5H_5N.HSO_4CH_3$     (A)

$2I^- \rightarrow I_2+2e^-$     (B)

In the water content measurement method using the infrared spectroscope, the water content of the sample is quantified by detection of an absorption peak of O—H stretching vibration of water at around 3000 to 4000 $cm^{-1}$ and an absorption peak of H—O—H deformation vibration of water at 1500 to 1700 $cm^{-1}$.

As one example of the water content measurement method based on the electric conductivity measurement, there is a method of quantifying the content of water (0.01 to 0.4%) in anhydrous hydrofluoric acid by measuring electric conductivity between platinum electrodes as defined by International Organization for Standardization (ISO) (see Non-Patent Document 2). It has also been reported, as another example, that the content of water in $SF_6$ is analyzed by electric conductivity measurement between electrodes (see Patent Document 1).

PRIOR ART DOCUMENTS

Patent Documents

Patent Document 1: Japanese Laid-Open Patent Publication No. 2006-308502

Non-Patent Documents

Non-Patent Document 1: Quantification of Water Content (Tokyo Kagaku Dojin, First Edition, P. 16)
Non-Patent Document 2: Draft. International Standard, ISO/DIS 3700.2 (1978)

SUMMARY OF THE INVENTION

Problems to be Solved by the Invention

However, it is difficult to accurately quantify the content of water in a compound containing hydrogen fluoride (hereinafter also referred to as "hydrogen fluoride-containing compound") by the above methods because of the following interference factors.
[1] In the Karl Fischer method, it is conceivable to adopt a water vaporization process due to the fact that a hydrogen-fluoride containing compound is difficult to dissolve in a Karl Fischer's solution. This process causes reaction between hydrogen fluoride and iodine in the Karl Fischer's solution.
[2] In the water content measurement method using the infrared spectroscope, the absorption peak of hydrogen fluoride overlaps the absorption peak of O—H stretching vibration of water at around 3000 to 4000 $cm^{-1}$.
[3] In the water content measurement method based on the electric conductivity measurement, the measurement result is influenced by impurities in the compound.

As discussed above, there has been reported no method for accurate water content quantification of the hydrogen fluoride-containing compound.

It is accordingly an object of the present invention to provide a method and device for accurately quantifying the content of water in a hydrogen fluoride-containing compound.

Means for Solving the Problems

As a result of extensive researches, the present inventors have found that it is possible to accurately quantify the content of water in a hydrogen fluoride-containing compound by causing thermal decomposition of the hydrogen fluoride-containing compound and analyzing the water content of the resulting thermal decomposition gas. The present invention is based on such a finding.

Namely, the present invention provides a water content measurement method for a hydrogen fluoride-containing compound represented by the general formula: XF.nHF (where X is either one of K, $NH_4$, Na and Li; and n is a rational number greater than 0), the water content measurement method comprising: causing thermal decomposition of the hydrogen fluoride-containing compound, thereby generating a thermal decomposition gas; and determining the water content of the hydrogen fluoride-containing compound by quantification of the water content of the thermal decomposition gas.

In the present measurement method, the water content of the thermal decomposition gas may be quantified by cooling the thermal decomposition gas to a liquid and measuring the electric conductivity of the liquid. Alternatively, the water content of the thermal decomposition gas may be quantified by Karl Fischer method after neutralizing the thermal decomposition gas with a base.

The present invention also provides a water content measurement device for a hydrogen fluoride-containing compound represented by the general formula: XF.nHF (where X is either one of K, $NH_4$, Na and Li; and n is a rational number greater than 0), the water content measurement device comprising: a thermal decomposition unit having a reaction vessel equipped with heating means for causing thermal decomposition of the hydrogen fluoride-containing compound; an introduction line arranged to introduce the hydrogen fluoride-containing compound into the thermal decomposition unit; a collection unit having a cooling trap for collecting hydrogen fluoride in a thermal decomposition gas generated by the thermal decomposition within the reaction vessel; an introduction line connected between the reaction vessel and the cooling trap to introduce the thermal decomposition gas from the reaction vessel into the cooling trap; a water content measurement unit having water content measurement means for measuring the water content of the collected hydrogen fluoride so as to determine the water content of the hydrogen fluoride-containing compound based on a measurement result of the water content measurement means; an introduction line connected between the cooling trap and the water content measurement means to introduce the collected hydrogen fluoride from the cooling trap into the water content measurement means; and pressure measurement means mounted to the introduction line between the reaction vessel and the cooling trap for measuring an increase in pressure caused by generation of the thermal decomposition gas.

In the present measurement device, the water content measurement means may be configured to quantify the water content of the hydrogen fluoride by measuring the electric conductivity of the hydrogen fluoride while keeping the hydrogen fluoride in liquid form.

Alternatively, the present measurement device may include: a neutralization unit having a neutralization chamber filled with a neutralization agent so as to neutralize the hydrogen fluoride; switching means coupled to the introduction line between the cooling trap and the water content measurement means for switching, from the water content measurement means to the neutralization chamber, a destination to which the hydrogen fluoride collected by the cooling trap is introduced; and an introduction line arranged to introduce a neutralization product generated by neutralization of the hydrogen fluoride with the base from the neutralization chamber into the water content measurement means so that the water content measurement means can quantify the water content of the neutralization product. In this case, it is feasible to adopt Karl Fischer method for water content quantification of the neutralization product.

Further, the pressure measurement means may be configured to stop the heating means upon receipt of a predetermined measurement result in the present measurement device.

DETAILED DESCRIPTION OF THE EMBODIMENTS

Figure 1:
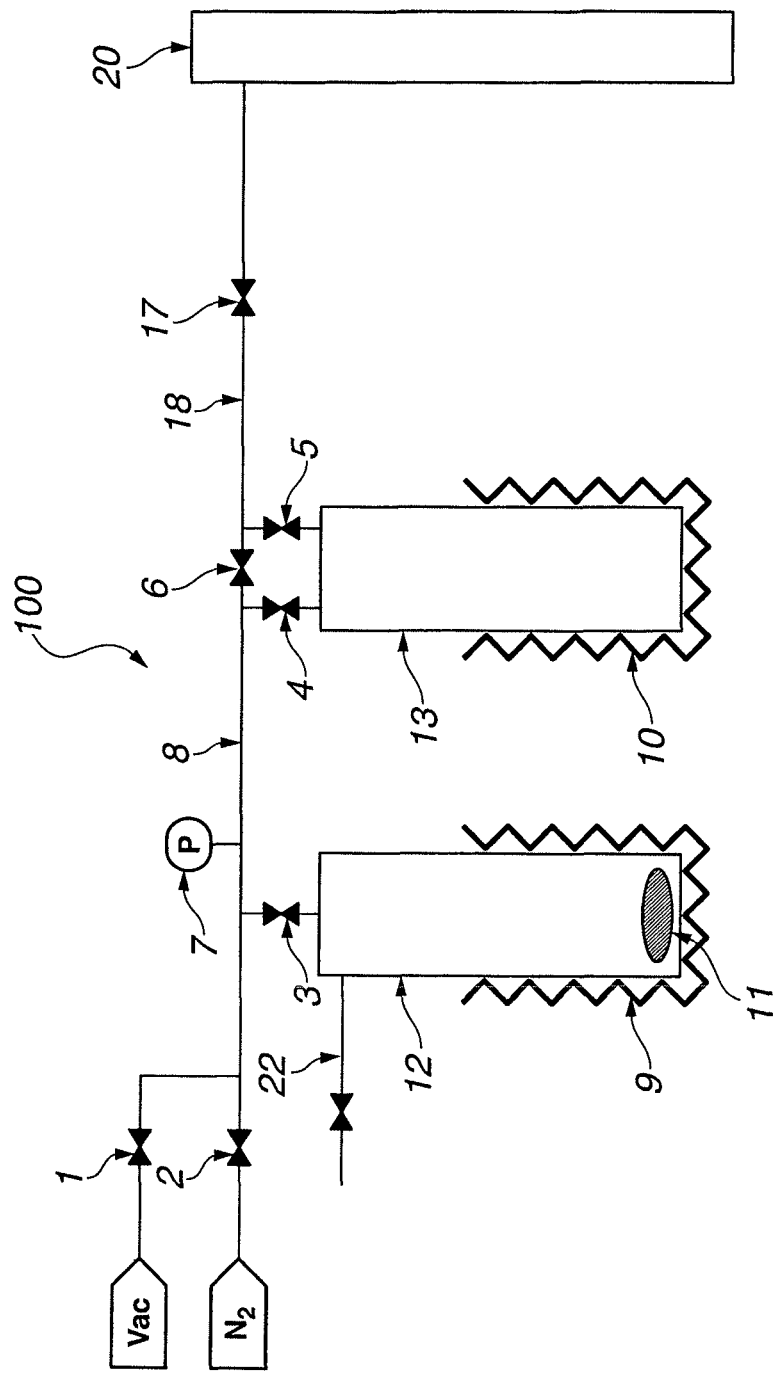
FIG. 1 is a schematic view of a water content measurement device according to a first embodiment of the present invention.

Hereinafter, the present invention will be described below in detail.

In the present invention, the water content of a hydrogen fluoride-containing compound of the general formula: $XF.nHF$ (where X is either one of K, $NH_4$, Na and Li; and n is a rational number greater than 0) is determined by causing thermal decomposition of the hydrogen fluoride-containing compound and quantifying the water content of a thermal decomposition gas generated by the thermal decomposition.

In the thermal decomposition, the heating temperature is preferably set higher than or equal to the boiling point of water or the decomposition temperature of the hydrogen fluoride-containing compound in order to completely evaporate water contained in the hydrogen fluoride-containing compound. In the case where X is K in the general formula: $XF.nHF$, for example, the heating temperature is preferably higher than or equal to 220° C., that is, the decomposition temperature of $KF.HF$. In the case where X is Na in the general formula: $XF.nHF$, the heating temperature is preferably higher than or equal to 270° C., that is, the decomposition temperature of $NaF.HF$. In the case where X is $NH_4$ in the general formula: $XF.nHF$, the heating temperature is preferably higher than or equal to 150° C., that is, the decomposition temperature of $NH_4F.HF$. In the case where X is Li in the general formula: $XF.nHF$, the heating temperature is preferably higher than or equal to 20° C., that is, the decomposition temperature of $LiF.HF$. If the heating temperature is at about the decomposition temperature, there is a possibility that the decomposition efficiency may deteriorate due to a low decomposition rate. If the heating temperature is too high, there is a possibility of damage to a reaction vessel in which the thermal decomposition take places. It is more preferable to set the heating temperature to within the range of 400 to 500° C. in the case where X is either one of K, Na and Li in the general formula: $XF.nHF$ and to within the range of 200 to 300° C. in the case where X is $NH_4$ in the general formula: $XF.nHF$.

In order to liquefy the thermal decomposition gas by cooling, it is necessary to cool the thermal decomposition gas at a temperature lower than or equal to the melting point (19° C.) of hydrogen fluoride that is a main component of the thermal decomposition gas. In the case where the hydrogen fluoride-containing compound is thermally decomposed into a solid phase and a gas phase (i.e. in the case where X is either one of K, Na and Li in the general formula: $XF.nHF$), it is also necessary to separate the thus-generated gas phase product from the solid phase product. The gas phase product may be extracted and separated by the use of an inert gas as a carrier gas. In this case, however, the carrier gas of controlled water content needs to be used or accurate water content quantification. It is thus preferable to extract and collect the thermal decomposition gas by cooling in a collecting trap etc. in order to efficiently separate the gas phase product. In the case of collecting the thermal decomposition gas by cooling in the collecting trap etc., the thermal decomposition gas is preferably cooled at a temperature lower than or equal to the freezing point (−84° C.) of hydrogen fluoride and thereby collected in solid form in terms of collection efficiency due to the fact that hydrogen fluoride in liquid form has a vapor pressure. When the thermal decomposition gas is collected in solid form, the thermal decomposition gas is brought into liquid form by heating at a temperature lower than or equal to the melting point (19° C.) of hydrogen fluoride.

It is feasible to adopt any known water content measurement method, such as water content measurement method based on electric conductivity measurement or Karl Fischer method, for water content quantification of the thermal decomposition gas.

In the case of quantifying the water content of the thermal decomposition gas by electric conductivity measurement, it is necessary to liquefy the thermal decomposition gas and measure the electric conductivity of the resulting liquid because the electric conductivity measurement of the gas is difficult to perform. The thermal decomposition gas is preferably liquefied by the above process.

When the water content of the thermal decomposition gas is measured by the electric conductivity measurement, the thus-obtained water content measurement result is converted to the water content of the hydrogen fluoride-containing compound, by multiplying the water content measurement result by a difference between the mass of the hydrogen fluoride-containing compound used for the water content measurement and the mass of the solid remaining after the removal of the thermal decomposition gas generated by the thermal decomposition, as indicated in the following conversion formula (1).

Water content measurement result×[(Mass of hydrogen fluoride-containing compound used for water content measurement)−(Mass of solid remaining after removal of thermal decomposition gas generated by thermal decomposition)]    (1)

In the case of quantifying the water content of the thermal decomposition gas by Karl Fischer method, it is necessary to neutralize the thermal decomposition gas with a base before the quantification. In the neutralization, the whole of the thermal decomposition gas needs to be reacted with the base.

Preferably, an organic base is used as the base in the neutralization. Particularly preferred examples of the organic base are amines such as trimethylamine, triethylamine, pyridine, bipyridine and tripyridine. In the case of using the amine as the organic base, the amount of the amine used is preferably 1 mole equivalent or more based on the total amount of the thermal decomposition gas. If the amount of the amine is less than 1 mole equivalent, there is a possibility of an error in the subsequent water content measurement due to insufficient neutralization of the thermal decomposition gas.

When the water content of the thermal decomposition gas (the water content of the neutralization product obtained by the neutralization of hydrogen fluoride in the thermal decomposition gas with the base) is measured by the Karl Fischer method, the thus-obtained water content measurement result is converted to the water content of the hydrogen fluoride-containing compound, by subtracting both of the mass of the hydrogen fluoride-containing compound used for the water content measurement and the mass of the solid remaining after the removal of the thermal decomposition gas generated by the thermal decomposition from the mass of the base used for the neutralization, and then, multiplying the water content measurement result by the resulting subtraction value, as indicated in the following conversion formula (2).

Water content measurement result×[(Mass of base used for neutralization)−(Mass of hydrogen fluoride-containing compound used for water content measurement)−(Mass of solid remaining after removal of thermal decomposition gas generated by thermal decomposition)]    (2)

It is feasible to more accurately quantify the water content of the thermal decomposition gas by preventing the entry of water from the outside during the above thermal decomposition step, cooling collection step and water content measurement step.

When n exceeds substantially 50 in the hydrogen fluoride-containing compound of the general formula: XF.nHF, the melting point of the hydrogen fluoride-containing compound is at the same level as that of hydrogen fluoride so that the hydrogen fluoride-containing compound can be handled in liquid form as in the case of hydrogen fluoride. In this case, the water content of the hydrogen fluoride-containing compound could conceivably be quantified by direct electric conductivity measurement without causing thermal decomposition. The accurate water content quantification of the hydrogen fluoride-containing compound is, however, difficult in the presence of the XF component. It is possible according to the present invention to separate the XF component by the thermal decomposition and accurately quantify the water content even by the water content measurement method based on the electric conductivity measurement. The water content of the hydrogen fluoride-containing compound could also conceivably be quantified by the Karl Fischer method after neutralizing the hydrogen fluoride-containing compound without causing thermal decomposition. However, the accurate water content quantification of the hydrogen fluoride-containing compound is difficult because the XF component remains undissolved after the neutralization. It is possible according to the present invention to separate the XF component by the thermal decomposition in the present invention and accurately quantify the water content even by the Karl Fischer method. In the case of adopting any method other than the electric conductivity measurement and the Karl Fischer method, the water content of the hydrogen fluoride-containing compound could conceivably directly be quantified without thermal decomposition. However, the accurate water content quantification of the hydrogen fluoride-containing compound is also difficult in the presence of the XF component. It is possible according to the present invention to separate the XF component by the thermal decomposition and accurately quantify the water content even by any method other than the electric conductivity measurement and the Karl Fischer method.

A water content measurement method and device for the hydrogen fluoride-containing compound according to a first embodiment of the present invention will be described below in detail with reference to FIG. 1.

The water content measurement device 100 of the first embodiment is structured to cause thermal decomposition of the hydrogen fluoride-containing compound, collect by cooling the resulting thermal decomposition gas and measure the water content of the thermal decomposition gas.

More specifically, the water content measurement device 100 includes: an introduction line 22 equipped with a valve; a thermal decomposition unit 12 for generating the thermal decomposition gas by thermal decomposition of the hydrogen fluoride-containing compound introduced through the introduction line 22; an introduction line 8 arranged to introduce the thermal decomposition gas from the thermal decomposition unit 12; a cooling trap 13 for collecting the thermal decomposition gas introduced through the introduction line 8 by cooling at the temperature lower than or equal to the freezing point (−84° C.) of hydrogen fluoride, and then, vaporizing the collected thermal decomposition gas by heating at the temperature higher than or equal to the melting point (19° C.) of hydrogen fluoride; an introduction line 18 arranged to introduce the vaporized thermal decomposition gas from the cooling trap 13; and water content measurement means 20 for measuring the water content of the thermal decomposition gas introduced through the introduction line 18. For gas replacement in the device system, a vacuum pump and a nitrogen gas feeding line are connected to the introduction line 8 via valves 1 and 2, respectively, and further connected to the thermal decomposition unit 12 via a valve 3. The introduction lines 8 and 18 are connected to each other via a valve 6 and are connected to the cooling trap 13 via valves 4 and 5, respectively. The introduction line 18 is also connected to the water content measurement means 20 via a valve 17. Further, the introduction line 8 is equipped with a pressure gauge 7.

The hydrogen fluoride-containing compound is sampled and stored into the thermal decomposition unit 12. The thermal decomposition unit 12 has a heater 9 for heating the hydrogen fluoride-containing compound. As the material of the thermal decomposition unit 12, it is preferable to use Monel metal, nickel, platinum, aluminum or the like that does not react with hydrogen fluoride in the generated thermal decomposition gas. Among others, Monel metal or nickel is particularly preferably used.

The cooling trap 13 has a cooler 10 for cooling the thermal decomposition gas. The cooler 10 can be of any type as long as it is capable of cooling the thermal decomposition gas to the temperature lower than or equal to the freezing point (−84° C.) of hydrogen fluoride during the collection. As the material of the cooling trap 13, it is preferable to use stainless steel, Monel metal, nickel, platinum, aluminum or the like. Among others, stainless steel or nickel is particularly preferably used.

The water content measurement means 20 may be provided as equipment capable of water content quantification by electric conductivity measurement. In the case where the hydrogen fluoride is contained in a small amount (at a low concentration level) in the thermal decomposition gas, the water content measurement means 20 may alternatively be provided as equipment capable of water content quantification by Karl Fischer method. It is preferable to use, as the water content measurement means 20, equipment for water content quantification by electric conductivity measurement in the case where a measurement accuracy of 1 mass ppm or lower is required.

Next, the operations of the water content measurement device 100 will be explained below.

The hydrogen fluoride-containing compound, taken as a sample for measurement, is introduced and stored into the thermal decomposition unit 12 through the introduction line 22 upon opening of the valve after the device system pressure is reduced to 0.1 kPa under gas replacement by the action of the vacuum pump and the nitrogen gas feeding line. After the storing, the valve on the introduction line 22 and the valves 1, 2, 5 and 6 are closed; and the valves 3 and 4 are opened. In this state, the thermal decomposition unit 12 is heated by the heater 9.

The heating temperature is preferably set higher than or equal to the boiling point of water or the decomposition temperature of the hydrogen fluoride-containing compound as mentioned above. In the case where X is K in the general formula: XF.nHF, the heating temperature is preferably higher than or equal to 220° C., that is, the decomposition temperature of KF.HF. In the case where X is Na in the general formula: XF.nHF, the heating temperature is preferably higher than or equal to 270° C., that is, the decomposition temperature of NaF.HF. In the case where X is $NH_4$ in the general formula: XF.nHF, the heating temperature is preferably higher than or equal to 150° C., that is, the decomposition temperature of $NH_4$F.HF. In the case where X is Li in the general formula: XF.nHF, the heating temperature is preferably higher than or equal to 20° C., that is, the decomposition temperature of LiF.HF. If the heating temperature is at about the decomposition temperature, there is a possibility that the decomposition efficiency may deteriorate due to a low decomposition rate. If the heating temperature is too high, there is a possibility of damage to a reaction vessel in which the thermal decomposition take places. It is more preferable to set the heating temperature to within the range of 400 to 500° C. in the case where X is either one of K, Na and Li in the general formula: XF.nHF and to within the range of 200 to 300° C. in the case where X is $NH_4$ in the general formula: XF.nHF.

Although the pressure is increased by generation of the thermal decomposition gas, the thermal decomposition gas is introduced into the cooling trap 13 through the introduction line 8 and collected in the cooling trap 8 by cooling at the temperature lower than or equal to the freezing point (84° C.) of hydrogen fluoride. When the reading of the pressure gauge 7 no longer exceeds 0.0 kPa, the valves 3 and 4 are closed. The heating operation of the thermal decomposition unit 12 is then stopped.

Subsequently, the cooling operation of the cooling trap 13 is stopped. The temperature of the cooling trap 13 is raised so that the collected gas is brought into liquid or gas form. The collected gas is taken out of the cooling trap 13 upon opening of the valves 5 and 17, and then, introduced into the water content measurement means 20 through the introduction line 18. The water content of the collected gas is measured by the water content measurement means 20. The thus-obtained water content measurement result of the water content measurement means 20 is converted to the water content of the hydrogen fluoride-containing compound. In this way, the water content of the hydrogen fluoride-containing compound is quantified.

As described above, it is possible according to the first embodiment of the present invention to accurately quantify the water content of the hydrogen fluoride-containing compound.

A water content measurement method and device for the hydrogen fluoride-containing compound according to a second embodiment of the present invention will be described below in detail with reference to FIG. 2.

The water content measurement device 200 of the second embodiment is structured to cause thermal decomposition of the hydrogen fluoride-containing compound, collect by cooling the resulting thermal decomposition gas, neutralize the collected thermal decomposition gas and quantify the water content of the thermal decomposition gas. The same parts of the water content measurement device 200 as those of the water content measurement device 100 are designated by the same reference numerals so as to omit explanations thereof for simplicity. The different parts of the water content measurement device 200 will be explained below.

In the water content measurement device 200, the introduction line 18 is branched at a position upstream of the valve 17. The water content measurement device 20 has a neutralization chamber 19 connected to the branched part of the introduction line 18 via a valve 14 and connected to the water content measurement means 20 via a valve 16 so as to freely select whether the gas is fed from the introduction line 18 into the water content measurement means 20 through or not through the neutralization chamber 19 by combination of open/close states of the valves 14 and 16.

The neutralization chamber 19 is filled with a neutralization agent so as to neutralize the hydrogen fluoride with the neutralization agent. The valve 14 is mounted to an inlet of the neutralization chamber 19 through which the vaporized gas is introduced from the cooling trap 13, whereas the valve 16 is mounted to an outlet of the neutralization chamber 19 through which the neutralized gas is discharged. A base is used as the neutralization agent. The base used is preferably an organic base. Among various organic bases, amines such as trimethylamine, triethylamine, pyridine, bipyridine and tripyridine are particularly preferred.

The introduction line 18 may be directly connected to the valve 14 without being branched. In this case, the introduction line 18 would not be directly connected to the water content measurement means 20.

The water content measurement means 20 can be provided as equipment capable of water content measurement by electric conductivity measurement or by Karl Fisher method. In the case of using equipment for water content measurement by Karl Fisher method, it is preferable to introduce the neutralization product from the neutralization chamber 19 into the water content measurement equipment in order to obtain a measurement accuracy of 1 mass ppm or lower. In the case of using equipment for water content measurement by electric conductivity measurement, the gas sample is introduced into the water content measurement means 20 without passing through the neutralization chamber 19.

Next, the operations of the water content measurement device 200 will be explained below. Explanations of the same operations of the water content measurement device 200 as those of the water content measurement device 100 will also be omitted; and the different operations of the water content measurement device 200 will be explained below.

The water content measurement device 200 operates in the same manner as the water content measurement device 100 until the stop of the cooling operation of the cooling trap 13. In the case of bypassing the neutralization chamber 19, the water content measurement device 200 operates in the same manner as the water content measurement device 100, except for closing the valve 14, until it quantifies the water content of the hydrogen fluoride-containing compound by conversion of the water content measurement result of the water content measurement means 20.

In the case of passing through the neutralization chamber 19, the temperature of the cooling trap 13 is raised to the temperature higher than equal to the boiling point (19° C.) of hydrogen fluoride so as to vaporize the collected gas after the cooling operation of the cooling trap 13 is stopped. Further, the valves 5 and 14 are opened; and the valves 16 and 17 are closed. The thermal decomposition gas generated by heating is fed through the introduction line 18, introduced into the neutralization chamber 19 through the valve 14 and neutralized with the neutralization agent within the neutralization chamber 19. The resulting liquid neutralization product is introduced into the water content measurement means 20 upon opening of the valve 16. The water content of the neutralization product is measured by the water content measurement means 20. The thus-obtained water content measurement result of the water content measurement means 20 is converted to the water content of the hydrogen fluoride-containing compound. In this way, the water content of the hydrogen fluoride-containing compound is quantified.

As mentioned above, it is possible in the second embodiment to obtain the same effects as those in the first embodiment and, even when the Karl Fischer method is adopted in the water content measurement means 20, quantify the water content of the hydrogen fluoride-containing compound more accurately. It is also possible to select the measurement accuracy as appropriate depending on the presence or absence of the neutralization treatment in the second embodiment.

EXAMPLES

The present invention will be described in more detail below by way of the following examples. It should be noted that the following examples are not intended to limit the present invention thereto.

Example 1

Figure 2:
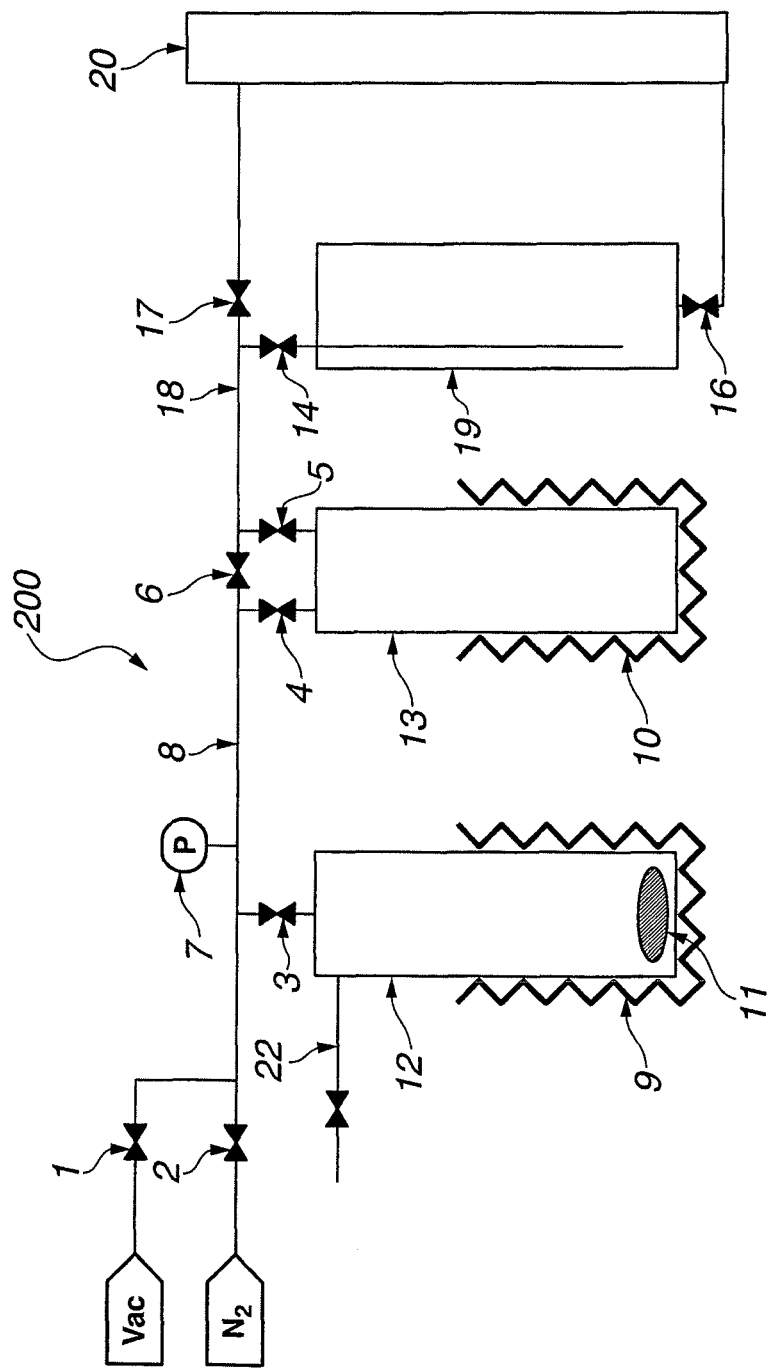
FIG. 2 is a schematic view of a water content measurement device according to a second embodiment of the present invention.

Using the device of FIG. 2, water content quantification test was performed by the following procedure.

In the present example, the thermal decomposition unit 12 was of the closed type and made of nickel; and the cooling trap 13 was made of nickel. As the hydrogen fluoride-containing compound 11, KF.HF having a water content of 123 mass ppm was prepared by mixing anhydrous KF, anhydrous HF and water. The anhydrous KF was produced by reacting $F_2$ with KF in such a manner as to convert the whole of $H_2O$ in KF to HF, and then, completely evaporating HF by heating at 700° C.; and the anhydrous HF was produced by reacting $F_2$ with HF in such a manner as to convert the whole of $H_2O$ in HF to HF, and then, degassing the resulting $O_2$ and $OF_2$. Further, the cooler 10 of the cooling trap 13 was of the type using liquid nitrogen as cooling medium; and the water content measurement means 20 was of the type adopting Karl Fisher method (available as "MKC-610-NT" from Kyoto Electronics Manufacturing Co., Ltd.).

By the action of the vacuum pump and the nitrogen gas feeding line connected to the thermal decomposition unit 12 via the valves 1 and 2, the thermal decomposition unit 12 was subjected to gas replacement in advance. Then, 10.2 g of the KF.HF containing 123 mass ppm of water was introduced as the hydrogen fluoride-containing compound 11 into the thermal decomposition unit 12 and heated at 220° C. by the heater 9. By closing the valve 5 and opening the valves 3 and 4, the thermal decomposition gas generated in the thermal decomposition unit 12 was introduced into the cooling trap 13 through the introduction line 8 and collected in the cooling trap 13 by cooling at −196° C. by the cooler 10. The heating operation of the thermal decomposition unit 12 was continued until the reading of the pressure gauge 7 on the introduction line 8 reached 0.0 kPa. After the pressure was reduced to 0.0 kPa, the valves 3 and 4 were closed. The heating operation of the thermal decomposition unit 12 was then stopped. The temperature of the cooling trap 13 was subsequently raised to 150° C., thereby vaporizing the collected gas. By opening the valves 5 and 14, the vaporized gas was introduced through the introduction line 18 into the neutralization chamber 19 in which a closed nickel vessel was filled with 40.0 g of dehydrated pyridine so as to neutralize hydrogen fluoride. The resulting neutralization product was introduced into the water content measurement means 20 by opening the valve 16. The water content of the neutralization product was measured by the water content measurement means 20.

The water content measurement value of the thermal decomposition gas was 481 mass ppm. The water content of the KF.HF, converted from the water content measurement value of the thermal decomposition gas, was 123 mass ppm.

Example 2

Water content quantification test was performed in the same manner as in Example 1, except that KF.2.2HF having a water content of 18.2 mass ppm was prepared by the same process as in Example 1 as the hydrogen fluoride-containing compound 11 to be tested and sampled in an amount of 15.3 g into the thermal decomposition unit 12; and the heating temperature of the heater 9 was set to 300° C.

The water content measurement value of the thermal decomposition gas was 42 mass ppm. The water content of the KF.2.2HF, converted from the water content measurement value of the thermal decomposition gas, was 18.1 mass ppm.

Example 3

Water content quantification test was performed in the same manner as in Example 1, except that KF.3.1HF having a water content of 13.2 mass ppm was prepared by the same process as in Example 1 as the hydrogen fluoride-containing compound 11 to be tested and sampled in an amount of 11.3 g into the thermal decomposition unit 12; and the heating temperature of the heater 9 was set to 400° C.

The water content measurement value of the thermal decomposition gas was 26 mass ppm. The water content of the KF.3.1HF, converted from the water content measurement value of the thermal decomposition gas, was 13.4 mass ppm.

Example 4

Water content quantification test was performed in the same manner as in Example 1, except that KF.2.2HF having a water content of 4461 mass ppm was prepared by the same process as in Example 1 as the hydrogen fluoride-containing compound 11 to be tested and sampled in an amount of 11.9 g into the thermal decomposition unit 12; and the heating temperature of the heater 9 was set to 450° C.

The water content measurement value of the thermal decomposition gas was 10352 mass ppm. The water content of the KF.2.2HF, converted from the water content measurement value of the thermal decomposition gas, was 4461 mass ppm.

Example 5

Water content quantification test was performed in the same manner as in Example 1, except that KF.0.7HF having a water content of 598 mass ppm was prepared by the same process as in Example 1 as the hydrogen fluoride-containing compound 11 to be tested and sampled in an amount of 20.9 g into the thermal decomposition unit 12; the heating temperature of the heater 9 was set to 450° C.; and triethylamine was used in place of pyridine.

The water content measurement value of the thermal decomposition gas was 3082 mass ppm. The water content of the KF.0.7HF, converted from the water content measurement value of the thermal decomposition gas, was 598 mass ppm.

Example 6

Water content quantification test was performed in the same manner as in Example 1, except that KF.5.1HF having a water content of 76.5 mass ppm was prepared by the same process as in Example 1 as the hydrogen fluoride-containing compound 11 to be tested and sampled in an amount of 14.2 g into the thermal decomposition unit 12; the heating temperature of the heater 9 was set to 500° C.; and triethylamine was used in place of pyridine.

The water content measurement value of the thermal decomposition gas was 120 mass ppm. The water content of the KF.5.1HF, converted from the water content measurement value of the thermal decomposition gas, was 76.5 mass ppm.

Example 7

Water content quantification test was performed in the same manner as in Example 1, except that KF.2.1HF having a water content of 1.8 mass ppm was prepared by the same process as in Example 1 as the hydrogen fluoride-containing compound 11 to be tested and sampled in an amount of 18.1 g into the thermal decomposition unit 12; the heating temperature of the heater 9 was set to 500° C.; and triethylamine was used in place of pyridine.

The water content measurement value of the thermal decomposition gas was 5.4 mass ppm. The water content of the KF.2.1HF, converted from the water content measurement value of the thermal decomposition gas, was 2.3 mass ppm.

Example 8

Water content quantification test was performed in the same manner as in Example 1, except that KF.2.1HF having a water content of 5.6 mass ppm was prepared by the same process as in Example 1 as the hydrogen fluoride-containing compound 11 to be tested and sampled in an amount of 13.5 g into the thermal decomposition unit 12; the heating temperature of the heater 9 was set to 450° C.; and the water content measurement means 20 used was of the type based on electric conductivity measurement (Miki and Maeno; Analytical Chemistry, 29, 288 (1980)) such that the collected gas was vaporized by raising the temperature of the cooling trap 13 to 150° C. and introduced into the water content measurement means 20, rather than the neutralization chamber 19, by closing the valves 14 and 16 and opening the valves 5 and 17, to measure the water content of the sample in a state where the sample was kept in liquid form by cooling down to −10° C.

The water content measurement value of the thermal decomposition gas was 13 mass ppm. The water content of the KF.2.1HF, converted from the water content measurement value of the thermal decomposition gas, was 5.5 mass ppm.

Example 9

Water content quantification test was performed in the same manner as in Example 8, except that KF.4.2HF having a water content of 102 mass ppm was prepared by the same process as in Example 1 as the hydrogen fluoride-containing compound 11 to be tested and sampled in an amount of 21.4 g into the thermal decomposition unit 12; and the heating temperature of the heater 9 was set to 400° C.

The water content measurement value of the thermal decomposition gas was 172 mass ppm. The water content of the KF.4.2HF, converted from the water content measurement value of the thermal decomposition gas, was 102 mass ppm.

Example 10

Water content quantification test was performed in the same manner as in Example 1, except that NaF.2.1HF having a water content of 7.5 mass ppm was sampled in an amount of 13.2 g as the hydrogen fluoride-containing compound 11 to be tested into the thermal decomposition unit 12; and the heating temperature of the heater 9 was set to 400° C. Herein, the NaF.2.1HF containing 7.5 mass ppm of water was prepared by mixing anhydrous NaF, anhydrous HF and water. The anhydrous NaF was produced by reacting $F_2$ with NaF in such a manner as to convert the whole of $H_2O$ in NaF to HF, and then, completely evaporating HF by heating to 700° C.; and the anhydrous HF was produced by reacting $F_2$ with HF in such a manner as to convert the whole of $H_2O$ in HF to HF, and then, degassing the resulting $O_2$ and $OF_2$.

The water content measurement value of the thermal decomposition gas was 15 mass ppm. The water content of the KF.2.1HF, converted from the water content measurement value of the thermal decomposition gas, was 7.5 mass ppm.

Example 11

Water content quantification test was performed in the same manner as in Example 1, except that NaF.3.1HF having a water content of 63.4 mass ppm was prepared by the same process as in Example 10 as the hydrogen fluoride-containing compound 11 to be tested and sampled in an amount of 20.1 g into the thermal decomposition unit 12; and the heating temperature of the heater 9 was set to 300° C.

The water content measurement value of the thermal decomposition gas was 106 mass ppm. The water content of the NaF.3.1HF, converted from the water content measurement value of the thermal decomposition gas, was 63.2 mass ppm.

Example 12

Water content quantification test was performed in the same manner as in Example 1, except that NaF.HF having a water content of 300 mass ppm was prepared by the same process as in Example 10 as the hydrogen fluoride-containing compound 11 to be tested and sampled in an amount of 15.5 g into the thermal decomposition unit 12; and the heating temperature of the heater 9 was set to 300° C.

The water content measurement value of the thermal decomposition gas was 931 mass ppm. The water content of the NaF.HF, converted from the water content measurement value of the thermal decomposition gas, was 300 mass ppm.

Comparative Example 1

As the hydrogen fluoride-containing compound 11, NaF.HF having a hydrogen content of 300 mass ppm was prepared in the same manner as in Example 12. Then, 1504 g of the NaF.HF was heated at 120° C. in a stainless desiccator so as to adsorb evaporated water by 9.35 g of molecular sieve 4A for 48 hours.

The mass of the molecular sieve was increased to 9.52 g. The amount of water adsorbed by the molecular sieve was 0.17 g. The water content of the NaF.HF, converted from the water adsorption amount, was 113 mass ppm.

The test results of the above examples are summarized in TABLE 1.

TABLE 1

| | Compound | Value n | Water content (mass ppm) of compound 11 | Mass (g) of compound 11 |
|---|---|---|---|---|
| Example 1 | KF•nHF | n = 1.0 | 123 | 10.2 |
| Example 2 | | n = 2.2 | 18.2 | 15.3 |
| Example 3 | | n = 3.1 | 13.2 | 11.3 |
| Example 4 | | n = 2.2 | 4461 | 11.9 |
| Example 5 | | n = 0.7 | 598 | 20.9 |
| Example 6 | | n = 5.1 | 76.5 | 14.2 |
| Example 7 | | n = 2.1 | 1.8 | 18.1 |
| Example 8 | | n = 2.1 | 5.6 | 13.5 |
| Example 9 | | n = 4.2 | 102 | 21.4 |
| Example 10 | NaF•nHF | n = 2.1 | 7.5 | 13.2 |
| Example 11 | | n = 3.1 | 63.4 | 20.1 |
| Example 12 | | n = 1.0 | 300 | 15.4 |
| Comparative Example 1 | | | | 1504 |

| | Measurement conditions | | | | |
|---|---|---|---|---|---|
| | Heating temp. (° C.) of heater 9 | Method of water content measurement means 20 | Kind of base used | Water content (mass ppm) of generated gas | Water content conversion value (mass ppm) |
| Example 1 | 220 | Karl Fischer method | pyridine | 481 | 123 |
| Example 2 | 300 | | | 42 | 18.1 |
| Example 3 | 400 | | | 26 | 13.4 |
| Example 4 | 450 | | | 10352 | 4461 |
| Example 5 | 450 | | triethylamine | 3082 | 598 |
| Example 6 | 500 | | | 120 | 76.5 |
| Example 7 | 500 | | | 5.4 | 2.3 |
| Example 8 | 450 | Electric conductivity measurement | — | 13 | 5.5 |
| Example 9 | 400 | | | 172 | 102 |
| Example 10 | 400 | Karl Fischer method | pyridine | 15 | 7.5 |
| Example 11 | 300 | | | 106 | 63.2 |
| Example 12 | 300 | Karl Fischer method | pyridine | 931 | 300 |
| Comparative Example 1 | 120 | Dry method | — | — | 113 |

It is clear from TABLE 1 that the water content of the hydrogen fluoride-containing compound was quantified more accurately in each of Examples 1 to 12 as compared with Comparative Example 1.

According to the present invention, it is possible to quantify the water content of the hydrogen fluoride-containing compound accurately as described above. The measurement method and device of the present invention can suitably be applied for the water content quantification of compounds such as KF.nHF and NH$_4$F.nHF usable as molten salts for electrolysis and compounds such as KF.HF and NaF.HF usable as fluorination agents.

Although the present invention has been described with reference to the above embodiments, various modifications and variations of the above embodiments can be made based on the knowledge of those skilled in the art without departing from the scope of the present invention.

The invention claimed is:

1. A water content measurement method for a hydrogen fluoride-containing compound represented by the general formula: XF.nHF (where X is either one of K, $NH_4$, Na and Li; and n is a rational number greater than 0), the water content measurement method comprising:
   causing thermal decomposition of the hydrogen fluoride-containing compound, thereby generating a thermal decomposition gas; and
   determining the water content of the hydrogen fluoride-containing compound by quantification of the water content of the thermal decomposition gas.

2. The water content measurement method for the hydrogen fluoride-containing compound according to claim 1, wherein the water content of the thermal decomposition gas is quantified by cooling the thermal decomposition gas to a liquid and measuring the electric conductivity of the liquid.

3. The water content measurement method for the hydrogen fluoride-containing compound according to claim 1, wherein the water content of the thermal decomposition gas is quantified by Karl Fischer method after neutralizing the thermal decomposition gas with a base.

4. A water content measurement device for a hydrogen fluoride-containing compound represented by the general formula: XF.nHF (where X is either one of K, $NH_4$, Na and Li; and n is a rational number greater than 0), the water content measurement device comprising:
   a thermal decomposition unit having a reaction vessel equipped with heating means for causing thermal decomposition of the hydrogen fluoride-containing compound;
   an introduction line arranged to introduce the hydrogen fluoride-containing compound into the thermal decomposition unit;
   a collection unit having a cooling trap for collecting hydrogen fluoride in a thermal decomposition gas generated by the thermal decomposition within the reaction vessel;
   an introduction line connected between the reaction vessel and the cooling trap to introduce the thermal decomposition gas from the reaction vessel into the cooling trap;
   a water content measurement unit having water content measurement means for measuring the water content of the collected hydrogen fluoride so as to determine the water content of the hydrogen fluoride-containing compound based on a measurement result of the water content measurement means;
   an introduction line connected between the cooling trap and the water content measurement means to introduce the collected hydrogen fluoride from the cooling trap into the water content measurement means; and
   pressure measurement means mounted to the introduction line between the reaction vessel and the cooling trap for measuring an increase in pressure caused by generation of the thermal decomposition gas.

5. The water content measurement device for the hydrogen fluoride-containing compound according to claim 4, further comprising:
   a neutralization unit having a neutralization chamber filled with a neutralization agent so as to neutralize the hydrogen fluoride;
   switching means coupled to the introduction line between the cooling trap and the water content measurement means for switching, from the water content measurement means to the neutralization chamber, a destination to which the hydrogen fluoride collected by the cooling trap is introduced; and
   an introduction line arranged to introduce a neutralization product generated by neutralization of the hydrogen fluoride with the base from the neutralization chamber into the water content measurement means so that the water content measurement means can quantify the water content of the neutralization product.

6. The water content measurement device for the hydrogen fluoride-containing compound according to claim 4, wherein the pressure measurement means is configured to stop the heating means upon receipt of a predetermined measurement result.

* * * * *